US012575874B2

(12) United States Patent
Mercier

(10) Patent No.: US 12,575,874 B2
(45) Date of Patent: Mar. 17, 2026

(54) CUTTING BLADE FOR VESSEL SEALER WITH KNIFE RETURN

(71) Applicant: Covidien LP, Mansfield, MA (US)

(72) Inventor: Daniel W. Mercier, Erie, CO (US)

(73) Assignee: Covidien LP, Mansfield, MA (US)

( * ) Notice: Subject to any disclaimer, the term of this patent is extended or adjusted under 35 U.S.C. 154(b) by 735 days.

(21) Appl. No.: 17/890,438

(22) Filed: Aug. 18, 2022

(65) Prior Publication Data

US 2023/0079193 A1     Mar. 16, 2023

Related U.S. Application Data

(60) Provisional application No. 63/242,512, filed on Sep. 10, 2021.

(51) Int. Cl.
*A61B 18/14*      (2006.01)
*A61B 18/00*      (2006.01)
*A61B 18/12*      (2006.01)

(52) U.S. Cl.
CPC ..... *A61B 18/1442* (2013.01); *A61B 2018/00589* (2013.01); *A61B 2018/00595* (2013.01);
(Continued)

(58) Field of Classification Search
CPC ....... A61B 17/28; A61B 17/285; A61B 17/29; A61B 17/295; A61B 18/1442; A61B 18/1445; A61B 2018/00345; A61B 2018/00589; A61B 2018/00595; A61B 2018/0063; A61B 2018/126; A61B 2018/1452; A61B 2018/1455
See application file for complete search history.

(56) References Cited

U.S. PATENT DOCUMENTS

D249,549 S    9/1978   Pike
4,164,225 A    8/1979   Johnson et al.
(Continued)

FOREIGN PATENT DOCUMENTS

EP      1645238 A1    4/2006
EP      1880685 A2    1/2008
(Continued)

OTHER PUBLICATIONS

Extended European Search Report No. 22194971.2 dated Feb. 1, 2023.

*Primary Examiner* — Khadijeh A Vahdat

(57)        ABSTRACT

A forceps includes a pair of jaw members movable relative to one another, one of the jaw members defining a blade channel therein configured to house a cutting mechanism. The cutting mechanism includes: a blade having camming slots defined along a length thereof and one or more blade springs operably associated therewith configured to bias the blade within the blade channel; and a blade cam including camming surfaces configured to operably engage the corresponding camming slots of the blade. The blade cam includes a proximal end operably coupled to an actuation rod configured to move the blade cam upon movement thereof. The actuation rod, upon movement thereof, moves the camming surfaces of the blade cam into engagement against the camming slots forcing the blade into the blade channel against the bias of the biasing spring to cut tissue therebetween.

18 Claims, 12 Drawing Sheets

(52) U.S. Cl.
CPC . *A61B 2018/0063* (2013.01); *A61B 2018/126*
(2013.01); *A61B 2018/1455* (2013.01)

(56) References Cited

U.S. PATENT DOCUMENTS

| | | | |
|---|---|---|---|
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 5,219,354 A | 6/1993 | Choudhury et al. | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,599,350 A | 2/1997 | Schulze et al. | |
| D384,413 S | 9/1997 | Zlock et al. | |
| 5,693,051 A | 12/1997 | Schulze et al. | |
| 5,755,717 A | 5/1998 | Yates et al. | |
| H1745 H | 8/1998 | Paraschac | |
| D402,028 S | 12/1998 | Grimm et al. | |
| 5,876,401 A | 3/1999 | Schulze et al. | |
| D408,018 S | 4/1999 | McNaughton | |
| D416,089 S | 11/1999 | Barton et al. | |
| 6,050,996 A | 4/2000 | Schmaltz et al. | |
| D424,694 S | 5/2000 | Tetzlaff et al. | |
| D425,201 S | 5/2000 | Tetzlaff et al. | |
| 6,113,598 A | 9/2000 | Baker | |
| H1904 H | 10/2000 | Yates et al. | |
| 6,174,309 B1 | 1/2001 | Wrublewski et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| 6,464,704 B2 | 10/2002 | Schmaltz et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| 7,033,356 B2 | 4/2006 | Latterell et al. | |
| 7,041,102 B2 | 5/2006 | Truckai et al. | |
| D525,361 S | 7/2006 | Hushka | |
| D531,311 S | 10/2006 | Guerra et al. | |
| 7,118,570 B2 | 10/2006 | Tetzlaff et al. | |
| 7,131,970 B2 | 11/2006 | Moses et al. | |
| D533,274 S | 12/2006 | Visconti et al. | |
| D533,942 S | 12/2006 | Kerr et al. | |
| D535,027 S | 1/2007 | James et al. | |
| 7,156,846 B2 | 1/2007 | Dycus et al. | |
| D538,932 S | 3/2007 | Malik | |
| D541,418 S | 4/2007 | Schechter et al. | |
| D541,611 S | 5/2007 | Aglassinge | |
| D541,938 S | 5/2007 | Kerr et al. | |
| D545,432 S | 6/2007 | Watanabe | |
| D547,154 S | 7/2007 | Lee | |
| 7,252,667 B2 | 8/2007 | Moses et al. | |
| 7,267,677 B2 | 9/2007 | Johnson et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,632,269 B2 | 12/2009 | Truckai et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 7,744,615 B2 | 6/2010 | Couture | |
| D621,503 S | 8/2010 | Otten et al. | |
| 7,811,283 B2 | 10/2010 | Moses et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 8,147,489 B2 | 4/2012 | Moses et al. | |
| 8,241,282 B2 | 8/2012 | Unger et al. | |
| 8,298,233 B2 | 10/2012 | Mueller | |
| 8,394,096 B2 | 3/2013 | Moses et al. | |
| 8,409,246 B2 | 4/2013 | Kerr et al. | |
| 8,409,247 B2 | 4/2013 | Garrison et al. | |
| 8,425,511 B2 | 4/2013 | Olson | |
| 8,430,877 B2 | 4/2013 | Kerr et al. | |
| 8,439,913 B2 | 5/2013 | Horner et al. | |
| 8,469,716 B2 | 6/2013 | Fedotov et al. | |
| 8,469,991 B2 | 6/2013 | Kerr | |
| 8,469,992 B2 | 6/2013 | Roy et al. | |
| 8,480,671 B2 | 7/2013 | Mueller | |
| 8,491,624 B2 | 7/2013 | Kerr et al. | |
| 8,491,625 B2 | 7/2013 | Horner | |
| 8,491,626 B2 | 7/2013 | Roy et al. | |
| 8,512,336 B2 | 8/2013 | Couture | |
| 8,540,749 B2 | 9/2013 | Garrison et al. | |
| 8,551,091 B2 | 10/2013 | Couture et al. | |
| 8,556,929 B2 | 10/2013 | Harper et al. | |
| 8,568,397 B2 | 10/2013 | Horner et al. | |
| 8,568,408 B2 | 10/2013 | Townsend et al. | |
| 8,585,736 B2 | 11/2013 | Horner et al. | |
| 8,597,295 B2 | 12/2013 | Kerr | |
| 8,623,018 B2 | 1/2014 | Horner et al. | |
| 8,628,557 B2 | 1/2014 | Collings et al. | |
| 8,641,712 B2 | 2/2014 | Couture | |
| 8,647,343 B2 | 2/2014 | Chojin et al. | |
| 8,652,135 B2 | 2/2014 | Nau, Jr. | |
| 8,663,222 B2 | 3/2014 | Anderson et al. | |
| 8,672,939 B2 | 3/2014 | Garrison | |
| 8,685,009 B2 | 4/2014 | Chernov et al. | |
| 8,685,021 B2 | 4/2014 | Chernov et al. | |
| 8,696,665 B2 | 4/2014 | Hunt et al. | |
| 8,702,749 B2 | 4/2014 | Twomey | |
| 8,734,445 B2 | 5/2014 | Johnson et al. | |
| 8,740,898 B2 | 6/2014 | Chojin et al. | |
| 8,745,840 B2 | 6/2014 | Hempstead et al. | |
| 8,757,467 B2 | 6/2014 | Racenet et al. | |
| 8,784,417 B2 | 7/2014 | Hanna | |
| 8,784,418 B2 | 7/2014 | Romero | |
| 8,795,269 B2 | 8/2014 | Garrison | |
| 8,808,288 B2 | 8/2014 | Reschke | |
| 8,814,864 B2 | 8/2014 | Gilbert | |
| 8,840,639 B2 | 9/2014 | Gerhardt, Jr. et al. | |
| 8,852,185 B2 | 10/2014 | Twomey | |
| 8,858,553 B2 | 10/2014 | Chojin | |
| 8,876,859 B2 | 11/2014 | Buehler et al. | |
| 8,888,771 B2 | 11/2014 | Twomey | |
| 8,888,775 B2 | 11/2014 | Nau, Jr. et al. | |
| 8,900,232 B2 | 12/2014 | Ourada | |
| 8,906,018 B2 | 12/2014 | Rooks et al. | |
| 8,920,421 B2 | 12/2014 | Rupp | |
| 8,932,293 B2 | 1/2015 | Chernov et al. | |
| 8,936,614 B2 | 1/2015 | Allen, IV | |
| 8,939,972 B2 | 1/2015 | Twomey | |
| 8,945,175 B2 | 2/2015 | Twomey | |
| 8,961,504 B2 | 2/2015 | Hoarau et al. | |
| 8,968,283 B2 | 3/2015 | Kharin | |
| 8,968,305 B2 | 3/2015 | Dumbauld et al. | |
| 8,968,316 B2 | 3/2015 | Roy et al. | |
| 8,968,357 B2 | 3/2015 | Mueller | |
| 8,968,359 B2 | 3/2015 | Kerr et al. | |
| 9,005,200 B2 | 4/2015 | Roy et al. | |
| 9,017,372 B2 | 4/2015 | Artale et al. | |
| 9,028,484 B2 | 5/2015 | Craig | |
| 9,028,495 B2 | 5/2015 | Mueller et al. | |
| 9,039,704 B2 | 5/2015 | Joseph | |
| 9,039,732 B2 | 5/2015 | Sims et al. | |
| D736,920 S | 8/2015 | Lee et al. | |
| 9,113,933 B2 | 8/2015 | Chernova et al. | |
| 9,113,934 B2 | 8/2015 | Chernov et al. | |
| 9,161,807 B2 | 10/2015 | Garrison | |

(56)          References Cited

U.S. PATENT DOCUMENTS

| | | | |
|---|---|---|---|
| 9,265,568 | B2 | 2/2016 | Chernov et al. |
| 9,333,002 | B2 | 5/2016 | Garrison |
| 9,381,059 | B2 | 7/2016 | Garrison |
| 9,456,870 | B2 | 10/2016 | Chernov et al. |
| 9,498,278 | B2 | 11/2016 | Couture et al. |
| 9,510,896 | B2 | 12/2016 | Sims et al. |
| 10,213,200 | B2 | 2/2019 | Kim et al. |
| 10,575,865 | B2 | 3/2020 | Sims et al. |
| 11,253,280 | B2 | 2/2022 | Kendrick |
| 11,304,717 | B2 | 4/2022 | Drochner et al. |
| 2002/0058965 | A1 | 5/2002 | Andrews |
| 2002/0107517 | A1 | 8/2002 | Witt et al. |
| 2003/0014053 | A1 | 1/2003 | Nguyen et al. |
| 2003/0171747 | A1 | 9/2003 | Kanehira et al. |
| 2003/0220637 | A1 | 11/2003 | Truckai et al. |
| 2003/0229344 | A1 | 12/2003 | Dycus et al. |
| 2005/0159745 | A1 | 7/2005 | Truckai et al. |
| 2006/0079891 | A1 | 4/2006 | Arts et al. |
| 2008/0021450 | A1* | 1/2008 | Couture ............. A61B 18/1442 |
| | | | 606/51 |
| 2008/0243106 | A1 | 10/2008 | Coe et al. |
| 2008/0319442 | A1 | 12/2008 | Unger et al. |
| 2009/0112246 | A1 | 4/2009 | Weisshaupt et al. |
| 2009/0157074 | A1 | 6/2009 | Livneh |
| 2010/0004208 | A1 | 1/2010 | Chaplin et al. |
| 2010/0228250 | A1 | 9/2010 | Brogna |
| 2010/0292691 | A1 | 11/2010 | Brogna |
| 2011/0004208 | A1 | 1/2011 | Truckai et al. |
| 2011/0193608 | A1 | 8/2011 | Krapohl |
| 2011/0270245 | A1 | 11/2011 | Horner et al. |
| 2011/0270251 | A1 | 11/2011 | Horner et al. |
| 2011/0276049 | A1 | 11/2011 | Gerhardt |
| 2011/0295313 | A1 | 12/2011 | Kerr |
| 2012/0059372 | A1 | 3/2012 | Johnson |
| 2012/0059409 | A1 | 3/2012 | Reschke et al. |
| 2012/0083786 | A1 | 4/2012 | Artale et al. |
| 2012/0083827 | A1 | 4/2012 | Artale et al. |
| 2012/0123404 | A1 | 5/2012 | Craig |
| 2012/0172868 | A1 | 7/2012 | Twomey et al. |
| 2012/0239034 | A1 | 9/2012 | Horner et al. |
| 2012/0265241 | A1 | 10/2012 | Hart et al. |
| 2012/0296205 | A1 | 11/2012 | Chernov et al. |
| 2012/0296238 | A1 | 11/2012 | Chernov et al. |
| 2012/0323238 | A1 | 12/2012 | Tyrrell et al. |
| 2012/0330308 | A1 | 12/2012 | Joseph |
| 2013/0018364 | A1 | 1/2013 | Chernov et al. |
| 2013/0022495 | A1 | 1/2013 | Allen, IV et al. |
| 2014/0128867 | A1 | 5/2014 | Collings et al. |
| 2016/0066981 | A1 | 3/2016 | Garrison |
| 2017/0071616 | A1* | 3/2017 | Sims .................. A61B 18/1442 |
| 2017/0348042 | A1 | 12/2017 | Drochner et al. |
| 2022/0039885 | A1 | 2/2022 | Hammerland, III et al. |

FOREIGN PATENT DOCUMENTS

| | | |
|---|---|---|
| EP | 2716239 A1 | 4/2014 |
| EP | 3266392 A2 | 1/2018 |
| WO | 2014120442 A2 | 8/2014 |

* cited by examiner

CUTTING BLADE FOR VESSEL SEALER WITH KNIFE RETURN

CROSS REFERENCE TO RELATED APPLICATION

This application claims the benefit of U.S. Provisional Application Ser. No. 63/242,512 filed Sep. 10, 2021, the entire contents of which being incorporated by reference herein.

BACKGROUND

Technical Field

The present disclosure relates to electrosurgical instruments used for open and endoscopic surgical procedures for sealing, fusing, or dividing tissue. More particularly, the present disclosure relates to bipolar forceps for sealing vessels, vascular tissues and soft tissues having a blade assembly which is designed to transect tissue while limiting movement of the cutting element.

Background

Electrosurgical forceps utilize both mechanical clamping action and electrical energy to effect hemostasis by heating the tissue and blood vessels to coagulate and/or cauterize vessels or tissue. However, certain surgical procedures may require sealing blood vessels or vascular tissue rather than just simply effecting hemostasis. "Vessel sealing" or "Tissue Fusion" is defined as the process of liquefying the collagen, elastin and ground substances in the tissue so that it reforms into a fused mass with significantly reduced demarcation between the opposing tissue structures. In contrast, the term "cauterization" is defined as the use of heat to destroy tissue (also called "diathermy" or "electrodiathermy") and the term "coagulation" is defined as a process of desiccating tissue wherein the tissue cells are ruptured and dried. Coagulation of small vessels is usually sufficient to permanently close them. Larger vessels or tissue need to be "sealed" to assure permanent closure. During sealing procedures, surgeons may also divide sealed tissue to ensure that the surrounding tissue heals properly.

Numerous electrosurgical instruments have been proposed in the past for various open and endoscopic surgical procedures. However, most of these instruments cauterize or coagulate tissue and are normally not designed to provide uniformly reproducible pressure on the blood vessel or tissue which, if used for sealing purposes, would result in an ineffective or non-uniform seal. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552, 143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cauterizing, and cutting vessels or tissue.

Many of these instruments include blade members or shearing members which simply cut tissue in a mechanical and/or electromechanical manner and are relatively ineffective for vessel sealing purposes. So far as it is known these blades are not designed or intended to transect tissue while limiting movement of the cutting element and end effector assembly. Other instruments generally rely on clamping pressure alone to procure proper sealing thickness and are often not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

Commonly-owned U.S. Application Serial Nos. PCT Application Serial No. PCT/US01/11340 filed on Apr. 6, 2001 by Dycus, et al. entitled "VESSEL SEALER AND DIVIDER", U.S. application Ser. No. 10/116,824 filed on Apr. 5, 2002 by Tetzlaff et al. entitled "VESSEL SEALING INSTRUMENT" and PCT Application Serial No. PCT/US01/11420 filed on Apr. 6, 2001 by Tetzlaff et al. entitled "VESSEL SEALING INSTRUMENT" teach that to effectively seal tissue or vessels, especially large vessels, two predominant mechanical parameters must be accurately controlled: 1) the pressure applied to the vessel; and 2) the gap distance between the conductive tissue contacting surfaces (electrodes). As can be appreciated, both of these parameters are affected by the thickness of the vessel or tissue being sealed. Accurate application of pressure is important for several reasons: to reduce the tissue impedance to a low enough value that allows enough electrosurgical energy through the tissue; to overcome the forces of expansion during tissue heating; and to contribute to the end tissue thickness which is an indication of a good seal.

As can be appreciated, considerable surgical skill is needed to determine what force is necessary and to accurately apply pressure to the treated tissue. In cases where tissue needs to be divided during the sealing process, the surgical difficulty is compounded by the use of blade assemblies that require lengthy movement such as longitudinal axial movement when the lower and upper jaw members are closed during the procedure. The long cutting motions are problematic in that they may lead to undesirable movement of the cutting element resulting in or promoting an inaccurate seal and/or division of tissue.

Thus, a need exists to develop an electrosurgical instrument which includes a cutting element assembly which can transect vessels and tissue consistently and effectively with minimal movement of the cutting element and end effector assembly.

SUMMARY

Provided in accordance with aspects of the resent disclosure is a forceps that includes a pair of jaw members movable from a first position in spaced relation relative to one another to one or more subsequent positions wherein the jaw members cooperate to grasp tissue therebetween. One (or both) of the jaw members has a blade channel defined therein configured to house a cutting mechanism therein, the cutting mechanism including: a blade having a series of camming slots defined along a length thereof, the blade including one or more blade springs operably associated therewith configured to bias the blade within the blade channel; and a blade cam disposed in general vertical registration with the blade, the blade cam including a series of camming surfaces configured to operably engage the corresponding series of camming slots of the blade, the blade cam including a proximal end operably coupled to an actuation rod configured to move the blade cam upon movement thereof.

Actuation of the actuation rod moves the camming surfaces of the blade cam into engagement against the camming slots forcing the blade into the blade channel against the bias of the one or more blade springs to cut tissue therebetween.

In aspects according to the present disclosure, upon release of the actuation rod, the bias of the blade spring returns the blade within the blade channel. In other aspects according to the present disclosure, the one jaw member includes a tissue engaging surface disposed thereon that defines the blade channel therein and wherein the one or more blade springs biases against an underside of the tissue engaging surface upon actuation of the actuation rod.

In aspects according to the present disclosure, the blade includes two blade springs on either side thereof that are each configured to engage the underside of the tissue engaging surface of the one jaw member upon actuation of the actuation rod. In other aspects according to the present disclosure, the blade includes a plurality of blade springs on either side thereof that are each configured to engage the underside of the tissue engaging surface of the one jaw member upon actuation of the actuation rod.

In aspects according to the present disclosure, the bias of the one or more blade springs operates to return the actuation rod upon release thereof.

In aspects according to the present disclosure, the blade includes a proximal end defining a slot therein configured to slide atop a pin operably associated with the one jaw member, the slot and pin arrangement configured to control the movement of the blade into the blade channel upon actuation of the actuation rod. In aspects according to the present disclosure, the slot and pin arrangement controls movement of the blade into the blade channel in a vertical direction towards the other jaw member. In yet other aspects according to the present disclosure, the slot and pin arrangement moves the blade both vertically and horizontally within the blade channel relative to the other jaw member to cut tissue disposed between the jaw members.

Provided in accordance with aspects of the resent disclosure is an electrosurgical forceps including a pair of jaw members movable from a first position in spaced relation relative to one another to one or more subsequent positions wherein the jaw members cooperate to grasp tissue therebetween. Each of the jaw members includes an electrically conductive sealing plate adapted to connect to an energy source and configured to communicate energy through tissue held therebetween. One (or both) of the jaw members has a blade channel defined therein configured to house a cutting mechanism therein, the cutting mechanism including: a blade having a series of camming slots defined along a length thereof, the blade including one or more blade springs operably associated therewith configured to bias the blade within the blade channel; and a blade cam disposed in general vertical registration with the blade, the blade cam including a series of camming surfaces configured to operably engage the corresponding series of camming slots of the blade, the blade cam including a proximal end operably coupled to an actuation rod configured to move the blade cam upon movement thereof.

Actuation of the actuation rod moves the camming surfaces of the blade cam into engagement against the camming slots forcing the blade into the blade channel and biasing the one or more blade springs against an underside of the electrically conductive sealing plate of the one jaw member to cut tissue disposed between the jaw members and wherein, upon release of the actuation rod, the bias of the one or more blade springs returns the blade into the blade channel.

In aspects according to the present disclosure, the blade includes two blade springs on either side thereof that are each configured to engage the underside of the electrically conductive sealing plate of the one jaw member upon actuation of the actuation rod. In aspects according to the present disclosure, the blade includes a plurality of blade springs on either side thereof that are each configured to engage the underside of the electrically conductive sealing plate of the one jaw member upon actuation of the actuation rod.

In aspects according to the present disclosure, the blade includes a proximal end defining a slot therein configured to slide atop a pin operably associated with the one jaw member, the slot and pin arrangement configured to control the movement of the blade into the blade channel upon actuation of the actuation rod. In other aspects according to the present disclosure, the slot and pin arrangement controls movement of the blade into the blade channel in a vertical direction towards the other jaw member. In still other aspects according to the present disclosure, the slot and pin arrangement moves the blade both vertically and horizontally within the blade channel relative to the other jaw member to cut tissue disposed between the jaw members.

Provided in accordance with aspects of the resent disclosure is a forceps that includes a pair of jaw members movable from a first position in spaced relation relative to one another to one or more subsequent positions wherein the jaw members cooperate to grasp tissue therebetween. One (or both) of the jaw members has a blade channel defined therein configured to house a cutting mechanism therein, the cutting mechanism including: a blade having a series of camming slots defined along a length thereof, the blade including a pair of blade springs disposed on either side thereof that are each configured to engage the underside of the tissue engaging surface of the one jaw member upon actuation of the actuation rod to bias the blade within the blade channel; and a blade cam disposed in general vertical registration with the blade, the blade cam including a series of camming surfaces configured to operably engage the corresponding series of camming slots of the blade, the blade cam including a proximal end operably coupled to an actuation rod configured to move the blade cam upon movement thereof.

Actuation of the actuation rod moves the camming surfaces of the blade cam into engagement against the camming slots forcing the blade into the blade channel against the bias of the pair of blade springs to cut tissue therebetween.

In aspects according to the present disclosure, the blade includes a plurality of pairs of blade springs disposed along a length thereof. In other aspects according to the present disclosure, the bias of the pair of blade springs operates to return the actuation rod upon release thereof.

DETAILED DESCRIPTION

It has been found that by providing a blade assembly where a blade body is in sliding communication with the blade channel, surgeons can more readily and more easily produce a consistent, high quality tissue transection while limiting movement of the blade and/or end effector assembly. By minimizing movement of the blade and/or end effector assembly during use the surgeon can more accurately divide and/or seal tissue. Furthermore, minimizing movement of the end effector assembly can also reduce thermal spread across or to adjacent tissue. For the purposes herein the term "thermal spread" refers generally to the heat transfer (heat conduction, heat convection or electrical current dissipation) dissipating along the periphery of the electrically conductive or electrically active surfaces to adjacent tissue. This can also be termed "collateral damage" to adjacent tissue.

It is envisioned that the configuration of the blade assembly, having a blade that is in sliding communication with at least one surface of the blade channel, will effectively minimize the movement of the blade by providing a predetermined cutting path. For the purposes herein the term "sliding communication" refers generally to two or more surfaces of different structures contacting one another such that the movement of one structure against a second structure will cause the moving structure or structures to move in one or more predetermined directions and/or sequentially in a plurality of directions. In other words, the shape of the surface of one structure will affect the path of movement of another structure sliding against it. Accordingly, in embodiments, the blade body has a predetermined shape which corresponds with the blade channel.

It is contemplated that by providing a shaped blade body and a shaped blade channel that the cutting path of the blade will be predetermined such that it influences the efficiency of the tissue cutting and/or limits the movement of the surgical device so that thermal spread/collateral damage to adjacent tissue structures is reduced or eliminated.

Figure 1A:
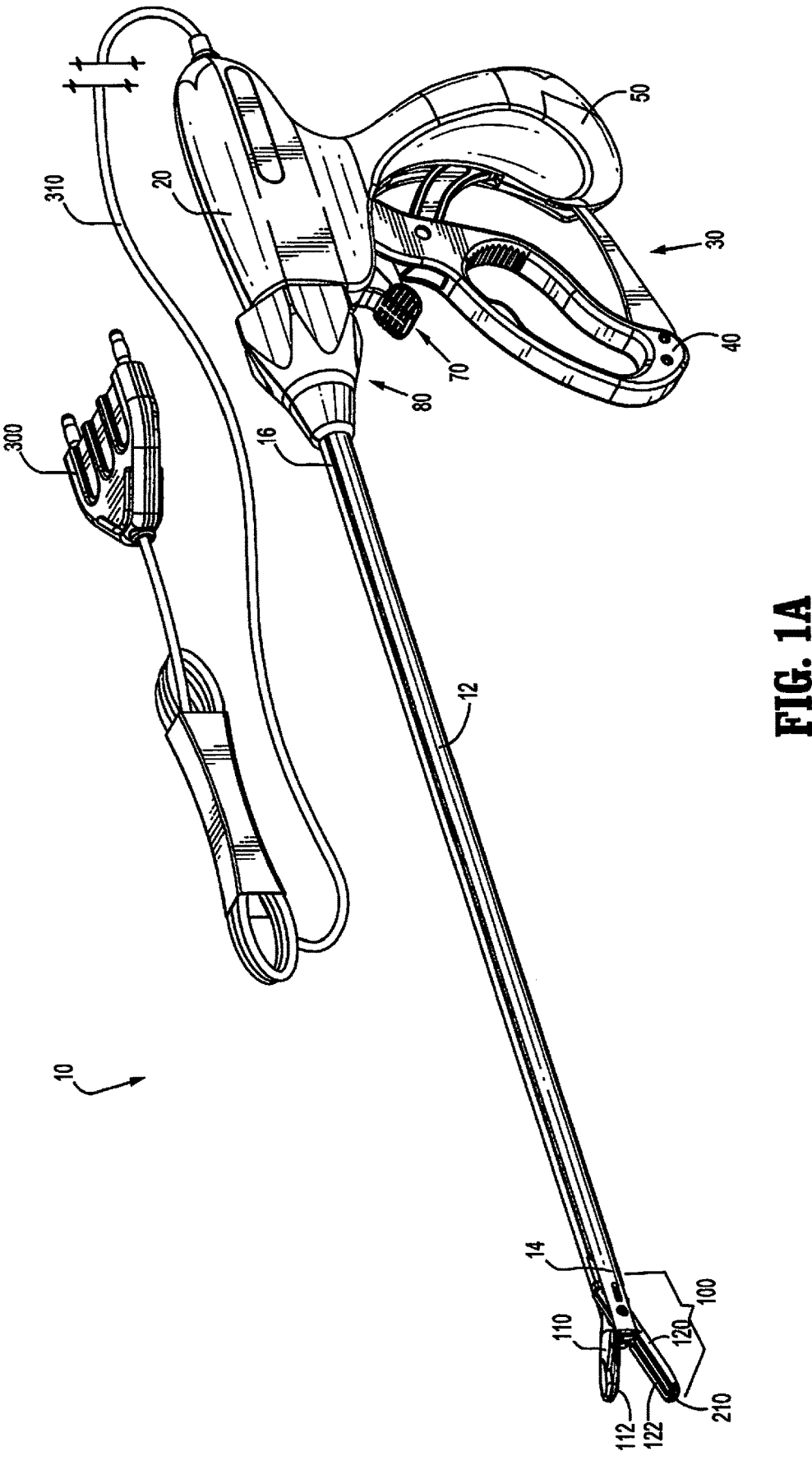
FIG. 1A is a perspective view of an endoscopic bipolar forceps which is configured to support the blade assembly according to the present disclosure.
Figure 1B:
FIG. 1B is a perspective view of an open bipolar forceps which is configured to support the blade assembly according to the present disclosure.

Referring now to FIG. 1A and FIG. 1B, two bipolar forceps 10 and 10' are shown; a first forceps 10 for use with endoscopic surgical procedures and a second forceps 10' for use with open surgical procedures. For the purposes herein, either an endoscopic instrument or an open instrument may be utilized for supporting the blade assembly according to the present disclosure. Obviously, different electrical and mechanical connections and considerations apply to each particular type of instrument, however, the novel aspects with respect to the blade assembly and its operating characteristics remain generally consistent with respect to both the open or endoscopic designs of FIGS. 1A and 1B. Forceps 10 and 10' are shown by way of example and other electrosurgical forceps are also envisioned which may support the blade assembly of the present disclosure. In the drawings and in the description which follows, the term "proximal", as is traditional, will refer to the end of the forceps 10, 10' which is closer to the user, while the term "distal" will refer to the end which is further from the user.

FIG. 1A shows one example of an endoscopic vessel sealing instrument 10 which is configured to support a blade assembly 200 (not shown in FIG. 1A). More particularly, forceps 10 generally includes a housing 20, a handle assembly 30, a rotating assembly 80, a trigger assembly 70 and the end effector assembly 100 which mutually cooperate to grasp, seal and, if warranted, divide tissue. The forceps 10 includes a shaft 12 which has a distal end 14 dimensioned to mechanically engage the end effector assembly 100 and a proximal end 16 which mechanically engages the housing 20 proximate the rotating assembly 80.

Forceps 10 also includes a plug 300 which connects the forceps 10 to a source of electrosurgical energy, e.g., an electrosurgical generator (not shown) via an electrical cable 310. Handle assembly 30 includes a fixed handle 50 and a movable handle 40. Handle 40 moves relative to fixed handle 50 to actuate the end effector assembly 100 and enable a user to grasp and manipulate tissue 400 (See FIGS. 8A-D). More particularly, the end effector assembly 100 includes a pair of opposing jaw members 110 and 120 which move in response to movement of the handle 40 from an open position wherein the jaw members 110 and 120 are disposed in spaced relation relative to one another, to a clamping or closed position wherein the jaw members 110 and 120 cooperate to grasp tissue therebetween.

The housing 20 encloses a drive assembly (not shown in FIG. 1A) which cooperates with the movable handle 40 to impart movement of the jaw members 110 and 120 from the open position to the clamping or closed position. The handle assembly 30 can generally be characterized as a four-bar mechanical linkage which provides a unique mechanical advantage when sealing tissue between the jaw members 110 and 120. For example, once the desired position for the sealing site is determined and the jaw members 110 and 120 are properly positioned, handle 40 may be compressed fully to lock the jaw members 110 and 120 in a closed position against the tissue. Further, should it be determined that tissue should be divided, trigger assembly 70 may be compressed to actuate the blade assembly in accordance with the present disclosure located in blade channel 210 in end effector assembly 100. Other force activating assemblies and trigger mechanisms are envisioned which may be used in connection with the blade assemblies described herein. The details relating to the inter-cooperative relationships of the inner-working components of various forceps 10 are disclosed in commonly-owned U.S. patent application Ser. No. 10/284, 562, U.S. patent application Ser. No. 10/460,926, and U.S. patent application Ser. No. 10/369,894 all of which are incorporated in their entirety by reference herein. When the jaw members 110 and 120 are fully compressed about the tissue, the forceps 10 is now ready for selective application of electrosurgical energy and/or tissue division.

Experimental results suggest that the magnitude of pressure exerted on the tissue by the electrically conductive sealing surfaces 112, 122 of the jaw members 110 and 120, respectively, is important in assuring a proper surgical seal. Pressures within a working range of about 3 kg/cm² to about 16 kg/cm² and, preferably, within a working range of about 6 kg/cm² to about 13 kg/cm² have been shown to be effective for sealing various tissue types. Pressures within a working range of about 4.5 kg/cm² to about 8.5 kg/cm² may be optimal for sealing particular tissue types.

An open forceps 10' for use in connection with traditional open surgical procedures and is shown by way of example in FIG. 1B. Open forceps 10' includes a pair of elongated shaft portions 12a', 12b' each having a proximal end 16a' and 16b', respectively, and a distal end 14a' and 14b', respectively. The forceps 10' includes jaw assembly 100' which attaches to the distal ends 14a' and 14b' of shafts 12a' and 12b', respectively. Jaw assembly 100' includes an upper jaw member 110' and a lower jaw member 120' which are movable relative to one another to grasp tissue therebetween.

Still referring to FIG. 1B, each shaft 12a' and 12b' includes a handle 17a' and 17b' disposed at the proximal end 16a' and 16b' thereof which each define a finger hole 18a' and 18b', respectively, therethrough for receiving a finger of the user. As can be appreciated, finger holes 18a' and 18b' facilitate movement of the shafts 12a' and 12b' relative to one another which, in turn, pivot the jaw members 110' and 120' from the open position wherein the jaw members 110' and 120' are disposed in spaced relation relative to one another for manipulating tissue to a clamping or closed position wherein the jaw members 110' and 120' cooperate to grasp tissue therebetween.

A ratchet 30' is included for selectively locking the jaw members 110' and 120' relative to one another at various positions during pivoting. In embodiments, each position associated with the cooperating ratchet interfaces 30' holds a specific, i.e., constant, strain energy in the shaft members 12a' and 12b' which, in turn, transmits a specific closing force to the jaw members 110' and 120'. It is envisioned that the ratchet 30' may include graduations or other visual markings which enable the user to easily and quickly ascertain and control the amount of closure force desired between the jaw members 110' and 120'. One of the shafts, e.g., 12b', includes a proximal shaft connector/flange 19' which is designed to connect the forceps 10' to a source of RF energy (not shown) via an electrosurgical cable 310 and plug 300. The details relating to the inner-working electrical connections and various envisioned forceps 10' are disclosed in commonly-owned U.S. patent application Ser. No. 10/962,166, U.S. patent application Ser. No. 10/991,157, and U.S. patent application Ser. No. 10/873,860, all of which are incorporated in their entirety by reference herein.

As mentioned above, two mechanical factors play an important role in determining the resulting thickness of the sealed tissue and effectiveness of the seal, i.e., the pressure applied between opposing jaw members 110' and 120' and the gap between the opposing jaw members 110' and 120' during the sealing process. Applying the correct force is also important for other reasons: to reduce the impedance of the tissue to a low enough value that allows enough current through the tissue; and to overcome the forces of expansion during the heating of the tissue in addition to contributing towards creating the required seal thickness necessary for a good seal.

For the purposes herein, electrode assemblies 100 and 100' include the same general configuration and are designed so that surgeons can more readily and more easily produce consistent, high quality tissue transections while limiting movement of the blade and/or end effector assembly. However, certain modifications may have to be made to each electrode sealing assembly 100 (or 100') to fit the electrode sealing assembly 100 (or 100') with blade assembly 200 to a specific support structure for an open or endoscopic instrument. By controlling the intensity, frequency and duration of the RF energy applied to the tissue, the user can selectively seal the tissue as needed for a particular purpose. As can be appreciated, different tissue types and the physical characteristics associated with each tissue type may require different electrical sealing and/or cutting parameters.

Figures 2A, 2B, 2C:
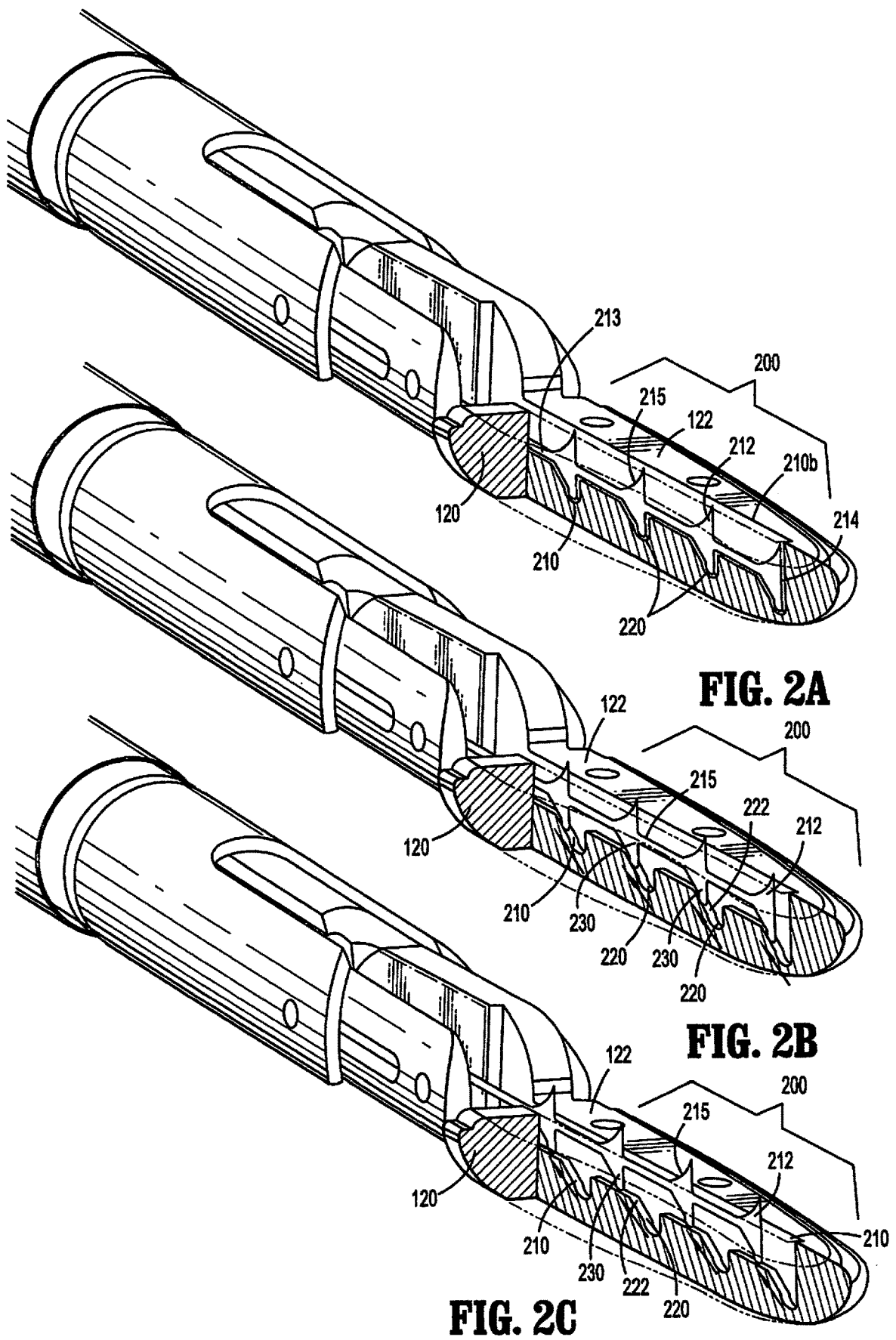
FIG. 2A is a greatly-enlarged, front perspective view of the bottom jaw member of the end effector assembly of FIG. 1A showing the blade of the blade assembly in a distal-most or unactuated position.
FIG. 2B is a greatly enlarged, front perspective view of the bottom jaw member of FIG. 1A showing the position of the blade after being slightly actuated.
FIG. 2C is a greatly enlarged, front perspective view of the bottom jaw member of FIG. 1A showing the position of the blade after being fully actuated in a proximal-most or fully actuated position.

FIGS. 2A, 2B and 2C show enlarged views of the lower jaw 120 of the electrode sealing assembly 100 (or 100')

according to the present disclosure. The front portion of lower jaw member 120 is cut away to show blade channel 210 in the center portion of the lower jaw member 120 below the lower sealing surface 122. As can be appreciated a second jaw 110 with similar components as described is positioned in opposition to jaw member 120. Only the elements of jaw member 120 are described herein, however, jaw member 110 may also include identical and/or similar elements which are designed to accomplish similar purposes such that bipolar electrosurgical energy can be conducted through tissue held between the two jaw members 110 and 120 to effect a seal and/or division of tissue. In the various discussed embodiments, the details relating to inner-working electrical connections and various components of lower jaw member 120 are disclosed in one or more of the above-mentioned commonly owned patent applications.

Referring now to FIG. 2A, lower jaw member 120 includes a blade assembly 200 in accordance with the present disclosure. The front portion of lower jaw member 120 is cut away to show blade channel 210 in the center portion of the lower jaw member 120 below the lower sealing surface 122. More particularly, lower jaw member 120 includes a blade assembly 200 having a blade channel 210 formed when the jaw members 110 (not shown in FIG. 2A) and 120 are closed. In other words, in embodiments, the blade channel 210 includes two blade channel halves—blade channel half 210a disposed in sealing plate 112 of jaw member 110 (not shown in FIG. 2A) and blade channel half 210b in sealing plate 122 of jaw member 120. Blade channel 210 extends through the longitudinal midline of jaw member 120. It is envisioned that the blade channel 210 may be configured as a straight slot with no degree of curvature, or alternatively, blade channel 210 may be dimensioned to include some degree of curvature. Blade channel 210 also includes one or more troughs 220 in the longitudinal bottom portion of blade channel 210. Recessed within the blade channel 210 lies blade 212 having a proximal end 213, a distal end 214, and a cutting edge 215 extending between the proximal and distal ends. As best seen in FIG. 2A, blade 212 is in a distal-most or unactuated position. Accordingly, the distal end 214 is in its distal-most position, and cutting edge 215 does not rise above or out of sealing surface 122.

Referring now to FIG. 2B, blade 212 is shown after being slightly actuated. More particularly, blade 212 is shown after being slightly actuated. More particularly, with respect to the blade movement, one or more flange 230 are positioned opposite cutting edge 215 of blade 212. Flange 230 of blade body 212 contacts the bottom of the blade channel 210 and is positioned in one or more troughs 220. It is envisioned that the trough 220 may be configured as a ramp with very little curvature. In other words, the proximal wall 222 of trough 220 may be a beveled edge. Alternatively, proximal wall 222 of trough 220 may be configured as a ramp with curvature. As seen in FIG. 2B, when blade assembly 200 is slightly activated, flange 230 moves proximally to a position immediately adjacent or upon proximal wall 222. Consequently, cutting edge 215 rises above or out of sealing surface 122.

Referring now to FIG. 2C, blade 212 is shown in a fully actuated position. More particularly, flange 230 of blade body 212 contacts the top of trough 220 or the most distal portion of proximal wall 222 of trough 220. As blade 212 is fully activated, and placed into its fully extended position, cutting edge 215 of the blade 212 moves up and out of lower sealing surface 122, as well as proximal to the distal edge of blade channel 210. It is envisioned that the blade can be moved in a first upwards direction to perforate tissue, then in a second proximal direction to cut across the tissue. Accordingly, the blade 212 and trough 220 may be dimensioned to move in one or more predetermined distances and/or directions depending on a particular purpose.

Figure 3A:
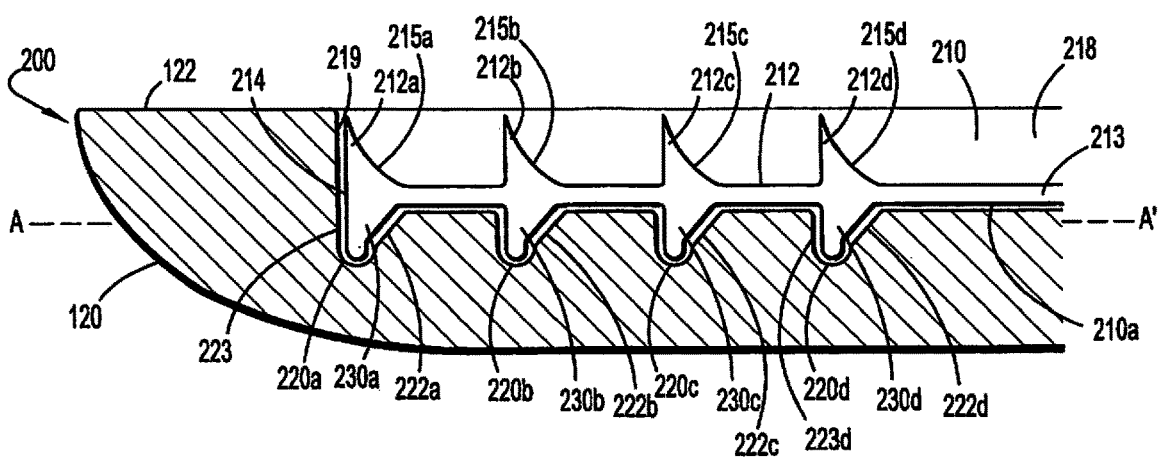
FIG. 3A is a schematic graphic illustration of the blade assembly of FIG. 2A in a distal-most or unactuated position.
Figure 3B:
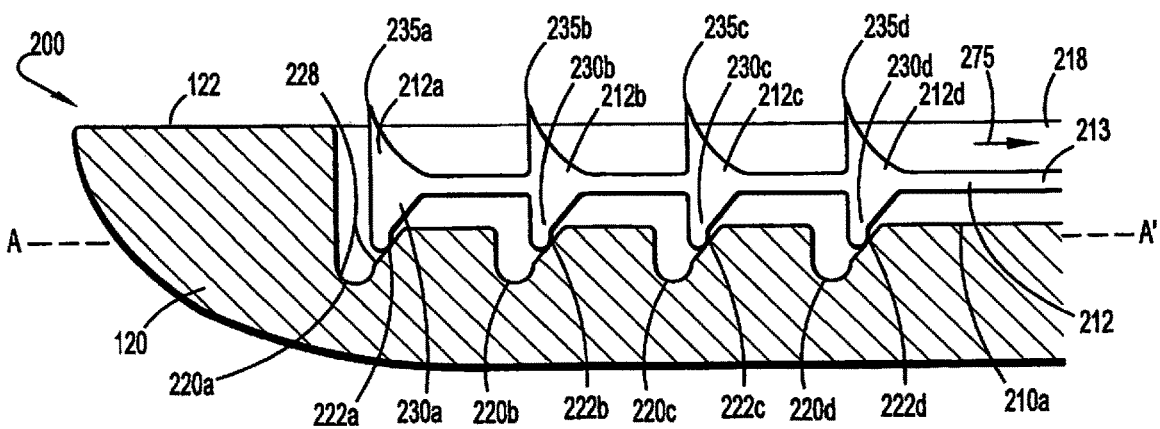
FIG. 3B is a schematic graphic illustration of the blade assembly of FIG. 2B showing the position of the blade after being slightly actuated.
Figure 3C:
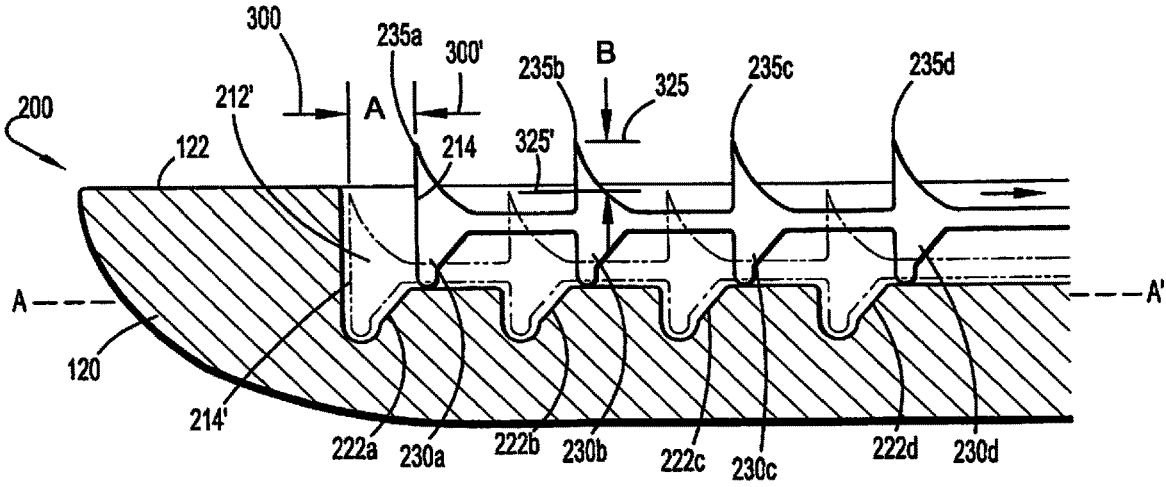
FIG. 3C is a schematic graphic illustration of the blade assembly of FIG. 2C showing the position of the blade after being fully actuated.

FIGS. 3A, 3B and 3C show enlarged schematic cross sectional side views of the lower jaw 120 of the electrode sealing assembly 100 (or 100') according to the present disclosure. Blade 212 may be dimensioned to include a plurality of individual cutting elements 212a, 212b, 212c and 212d disposed along the blade shaft of blade body 212. As can be appreciated any number of cutting elements 212a-212x may be utilized to suit a particular surgical purpose. Likewise, a corresponding number of blade troughs 220a-d may be utilized to cooperate with the cutting elements 212a-212d to transect tissue.

With particular respect to FIGS. 3A-3C, a single cutting element 212a and trough 222a will be explained in detail along with the operations thereof. As mentioned above, blade assembly 200 includes a blade channel defined therein. Blade channel 210 is shown having a proximal end 218, a distal end 219 and one or more troughs 220a-220d positioned between the proximal and distal ends. In each trough, for example, trough 220d has a corresponding proximal wall 222d, a distal wall 223d, and a predetermined depth. It is envisioned that the proximal wall 222d of trough 220d has a predetermined shape and/or may be configured as a straight edge with no degree of curvature. Alternatively, proximal wall 222d of the trough 220d may be dimensioned to include some degree of curvature. Blade body 212 includes a proximal end 213, a distal end 214, and a cutting element 212a-212d extending between the proximal and distal ends. Each cutting element 212a-212d includes a flange 230a-230d positioned opposite a corresponding cutting edge 215a-215d. Flanges 230 are disposed adjacent corresponding troughs 220 such that each cutting element 212a-212d is in sliding communication with the channel 210. Accordingly, movement of blade 212 in a proximal direction will cause flange 230a-230d to slide against the proximal walls of the troughs 222a-222d causing the cutting element 212a-212d to move in one or more predetermined directions and/or sequentially in a plurality of directions.

Referring now to FIG. 3A, blade 212 is in a distal-most or unactuated position. Accordingly, the distal end 214 is in its distal-most position and immediately adjacent to the distal end 219 of blade channel 210. Consequently, cutting edge 215 does not rise above or out of sealing surface 122.

Referring now to FIG. 3B, as the blade is actuated, flanges 230a-230d contact proximal ends 222a-222d of troughs 220a-220d. In one envisioned embodiment, trough 220 may be configured to have a receptacle 228 at the bottom portion thereof. In other words, the bottom of trough 220 may be rounded such that flange 230a-230d rest within the trough 220a-220d when the cutting elements are unactuated, and quickly extend the cutting elements 212a-212d into the tissue when the blade 212 is actuated. For example, the rounded portion of the troughs may have an incline of about 50 degrees to 90 degrees off of the longitudinal central axis A-A' to initially urge the blade into tissue. The proximal ends of the troughs may have an incline of about 10 degrees to 70 degrees off of the longitudinal central axis A-A' to facilitate cutting.

Moreover, different troughs, e.g. trough 220a, may have a different initial angle than another trough 220d. Still referring to FIG. 3B, when the blade 212 and blade channel 210 are in sliding communication, blade 212 is directed in at least two sequential directions when actuated in a proximal direction as shown by arrow 275. For example, initial activation may direct blade 212 in a first direction which may be substantially upward, and sequential activation may direct blade 212 in a substantially proximal direction. Accordingly, the predetermined shape of troughs 220a-220d will cause the blade to move in one or more predetermined directions. It is envisioned that proximal wall 222 may have many shapes, inclines, and depths in order to direct blade 212. In this case, activation in the direction of arrow 275 causes cutting points 235a-235d to rise above or out of sealing surface 122. As best shown in FIG. 8C, this initial first movement is well suited for puncturing tissue disposed upon lower sealing surface 122.

Referring now to FIG. 3C, compressing movement of the activator 70 (not shown in FIG. 3C) moves blade 212 to a proximal-most position to complete the cutting stroke. As such, flanges 230a-230d are pushed to the top of proximal wall of trough 222a-222d. Blade 212' is shown in phantom to show the difference between an unactuated blade 212 (FIG. 3A) and a fully actuated blade (FIG. 3C). As shown by distance "A" between arrow 300 and 300', the distal edge 214 moves in a proximal direction. Distance A may be in the range of about 5 mm to about 1 cm. As shown by distance "B" between arrow 325 and 325', the cutting points 235a-235d move in an upward direction in a range of about 5 mm to about 1 cm.

FIGS. 4A, 4B, 4C and 4D show enlarged schematic side views of the various blades 312, 412, 512, and 612 of the electrode sealing assembly 100 (or 100') according to the present disclosure. For example, blade 312 has a predetermined shape having a top cutting edge 315 and a bottom edge 357 that corresponds with the blade channel 310 (not shown). The length of the blade 312 is also predetermined depending on factors such as the size of the end effector assembly it will be assembled into and/or the type of tissue the forceps are suitable for cutting. In embodiments, the length of the blade is selected to fit effector assembly having jaws the length of about 3.5 cm.

In embodiments, blade 312 has a length of about 0.5 cm to about 5 cm. It is envisioned that the blade 312 may be configured to have one or more cutting elements 316, which extend away from the central longitudinal axis A-A' of the cutting blade 312. Each cutting element may have a substantially flat face 317 that extends from the blade body 312, the flat face terminating at a cutting point 335. The flat face has a width that is thin enough to be recessed inside the blade channel 310 (not shown in FIGS. 4A, 4B, 4C and 4D). The flat face may have a width of from about 1 mm to about 100 mm. In embodiments, the flat face may have a width of from about 10 mm to about 30 mm. The flat face has a second cutting edge 340 positioned between the cutting point 335 and the top of the blade shaft 385. The proximal edge of the flat face may have a sharp edge to form a second cutting edge 340. It is envisioned that the second cutting edge 340 may be configured as a straight edge with no degree of curvature between the cutting point and the top of the blade shaft 385. Alternatively, second cutting edge may be dimensioned to include some degree of curvature between the cutting point 340 and the top of the blade shaft 385.

It is envisioned that the blade 312 may be configured to have one or more flanges 330, which extend away from the central longitudinal axis A-A' of the cutting blade 312. Each flange may have a substantially flat surface 332 and extend from the blade body 312, the flat surface terminating at an edge or point 334. The flat surface has a width that is thin enough to be recessed inside the blade channel 310 (not shown in FIGS. 4A, 4B, 4C and 4D). In some embodiments, the flat surface may have a width of from about 1 mm to about 100 mm. In some embodiments, the flat surface may have a width of from about 10 mm to about 30 mm. The flat surface has a proximal edge 350 positioned between the edge or point 334 and the bottom of the blade shaft 390. It is envisioned that the proximal edge of the flange 350 may be configured as a straight edge with no degree of curvature between the edge or point 334 and the bottom of the blade shaft 390. Alternatively, proximal edge of the flange 350 may be dimensioned to include some degree of curvature between the cutting point and the bottom of the blade shaft 390.

Figures 4A, 4B, 4C, 4D:
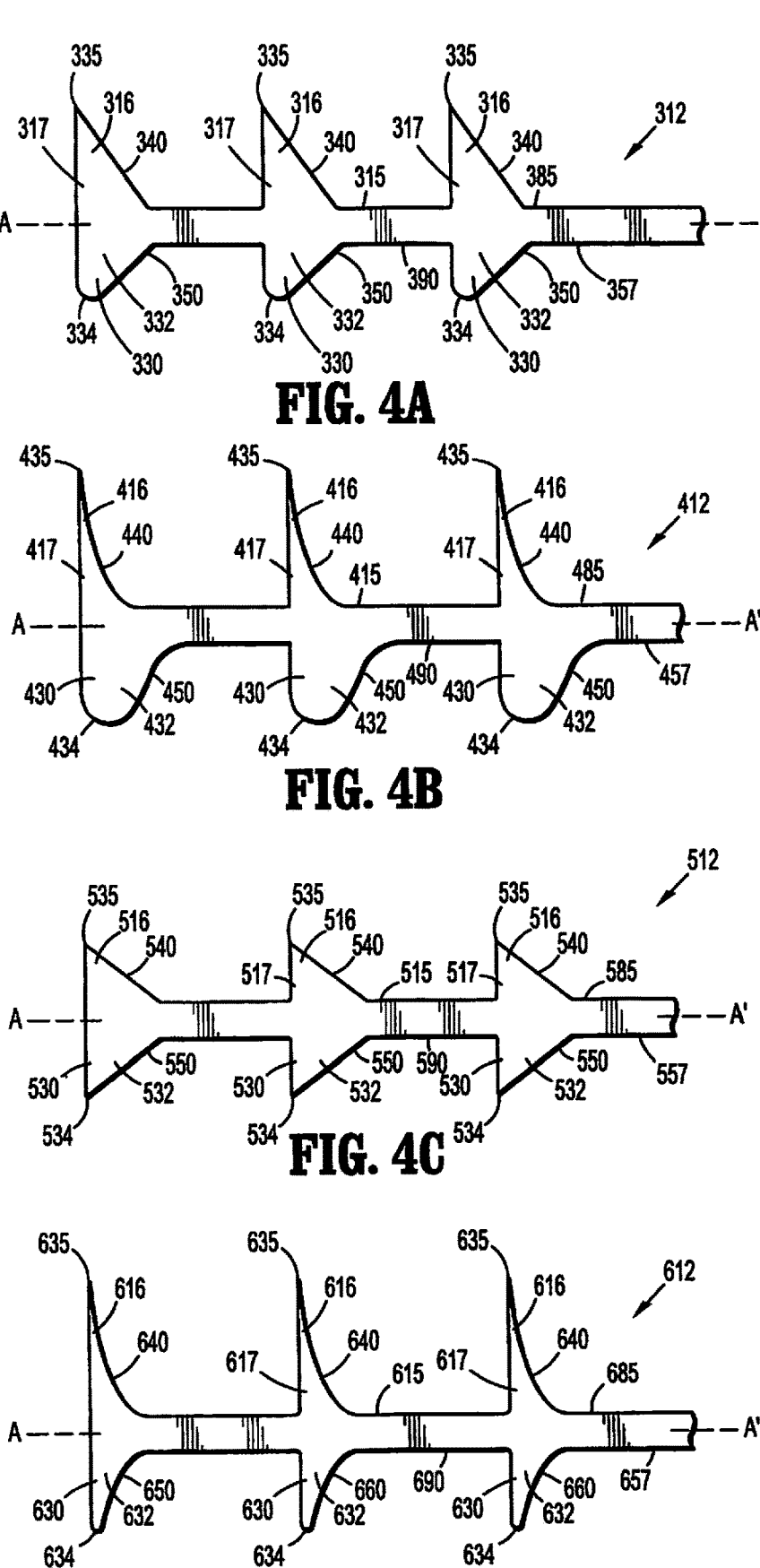
FIG. 4A is a side view of a first blade suitable for use in accordance with the present disclosure.
FIG. 4B is a side view of a second blade suitable for use in accordance with the present disclosure.
FIG. 4C is a side view of a third blade suitable for use in accordance with the present disclosure.
FIG. 4D is a side view of a fourth blade suitable for use in accordance with the present disclosure.

Referring now to FIG. 4A, the flat face 317 has a second cutting edge 340 positioned between the cutting point 335 and the top of the blade shaft 385. In other words, the proximal edge of the flat face 317 has a sharp edge forming a second cutting edge 340. Here second cutting edge 340 is configured as a straight edge with substantially no degree of curvature between the cutting point 335 and the top of the blade shaft 385. Further, the flat surface of the flange 330 has a proximal edge 350 positioned between the edge or point 334 and the bottom of the blade shaft 390. The proximal edge of the flange 350 is configured as a straight edge with substantially no degree of curvature between the edge 334 and the bottom of the blade shaft 390. Edge 334 is also shown as a substantially round or curved edge.

Referring now to FIG. 4B, an enlarged schematic side view of another blade 412 of the electrode sealing assembly 100 (or 100') according to the present disclosure is shown. The shape and dimensions of the blade is predetermined in that the cutting edge, number of cutting teeth, and troughs may vary depending on a number of factors, including, the types of tissue to be cut, dimensions of the jaw member, and dimensions of the blade channel (not shown in FIG. 4B). Here the blade 412 has more than one cutting teeth 416 extending from the longitudinal axis of the blade; more specifically three teeth extend from the axis A-A'. However it is envisioned that a plurality of cutting teeth may extend from axis A-A' such as 1 to 50 cutting teeth 416. Still referring to FIG. 4B, blade 412 has a corresponding number of flanges extending from the longitudinal axis of the blade A-A', more specifically three flanges extend from the axis. It is envisioned that the number of flanges 430 may be different than the number of cutting edges 416.

The flat face 417 has a second cutting edge 440 positioned between the cutting point 435 and the bottom of the top of the blade shaft 485. The proximal edge of the flat face 417 has a sharp edge forming a second cutting edge 440. The second cutting edge 440 is configured as a substantially curved edge with substantially a high degree of curvature between the cutting point and the longitudinal axis A-A'. Further, the flat surface 445 of the flange has a proximal edge 450 positioned between the edge or point 434 and the bottom of the blade shaft 490. The proximal edge of the flange 450 is configured as a curved edge with a substantially high degree of curvature between the edge 434 and the longitudinal axis A-A' of the blade such that an arc is formed having a proximal center. Edge 434 is also shown as a substantially round or curved edge.

Referring now to FIG. 4C, another embodiment of blade 512 is shown. The second cutting edge 540 is configured as a substantially straight edge with substantially no degree of curvature between the cutting point and the top of the blade shaft 585. Furthermore, the flat surface of the flange has a proximal edge 550 positioned between the edge or point 534 and the bottom of the blade shaft 590. The proximal edge of the flange 550 is configured as a straight edge with no degree of curvature between the edge 534 and the bottom of the blade shaft 590. Edge 534 is also shown as a point.

Referring now to FIG. 4D, yet another envisioned blade design 612 is shown. The second cutting edge 640 is configured as a substantially curved edge with substantially a high degree of curvature between the cutting point 635 and the top of the blade shaft 685 such that an arc is formed having a distal center. Furthermore, the flat surface of the flange has a proximal edge 650 positioned between the edge or point 634 and the bottom of the blade shaft 690. The proximal edge of the flange 650 is configured as a curved edge with a substantially high degree of curvature between the edge 634 and the bottom of the blade shaft 690 such that an arc is formed having a distal center. Edge 634 is also shown as a substantially round or curved edge.

Figure 5:
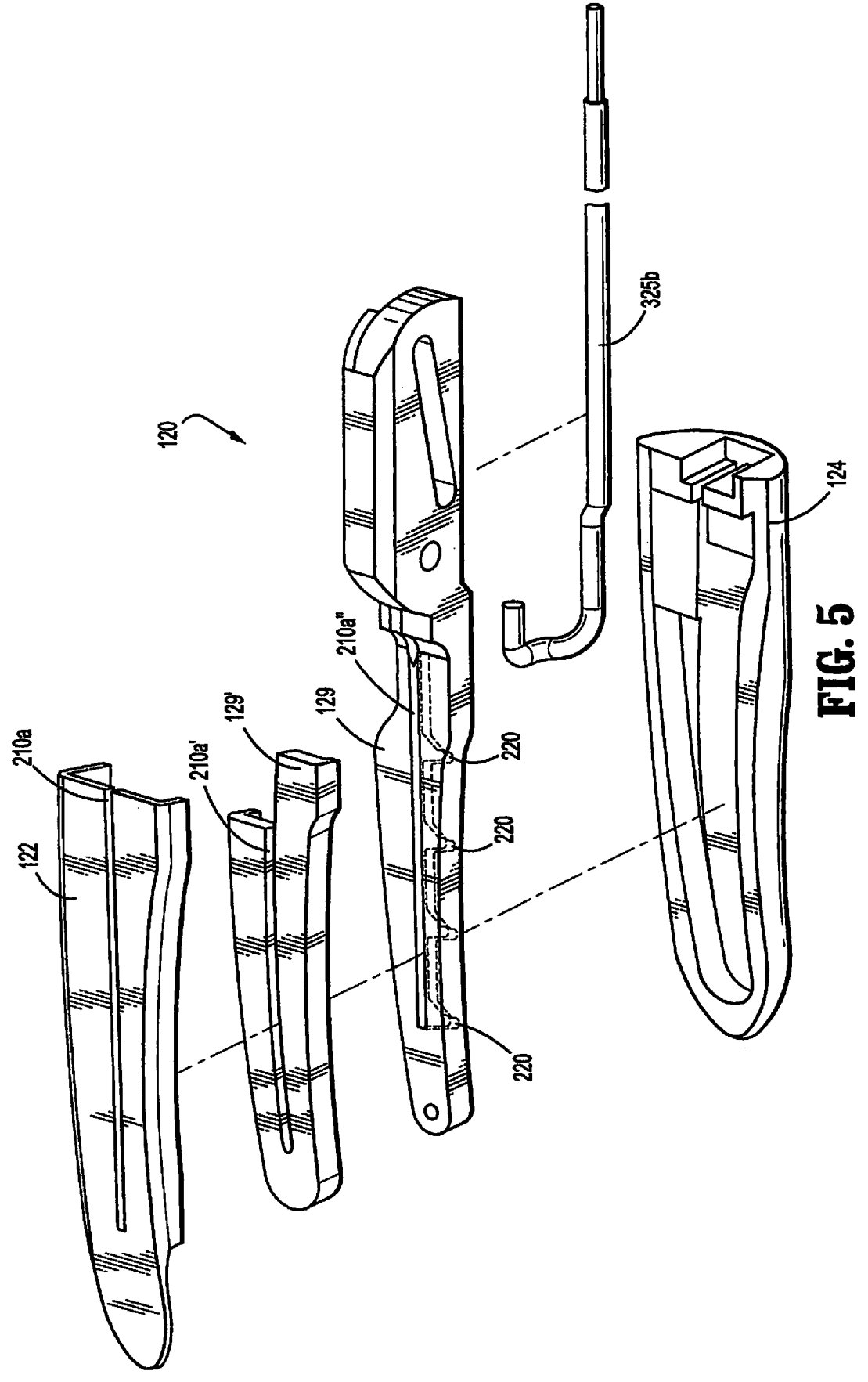
FIG. 5 is a greatly-enlarged, perspective view of the bottom jaw of the end effector assembly of FIG. 1A with parts separated.

As illustrated in FIG. 5, jaw member 120 includes a jaw housing 124 which encapsulates a support plate 129, an insulator plate 129' and an electrically conductive sealing surface 122. Likewise, the electrically conductive surface 122, insulator plate 129', and support plate 129 when assembled, include respective longitudinally-oriented blade channels 210a, 210a', and 210a" defined therethrough for reciprocation of the blade 212 (not shown in FIG. 5). As best seen in FIG. 5, the bottom of plate channel 210a is formed from the surface of support plate 129. Accordingly, troughs 220 are cut out of the surface of support plate 129.

Figure 6:
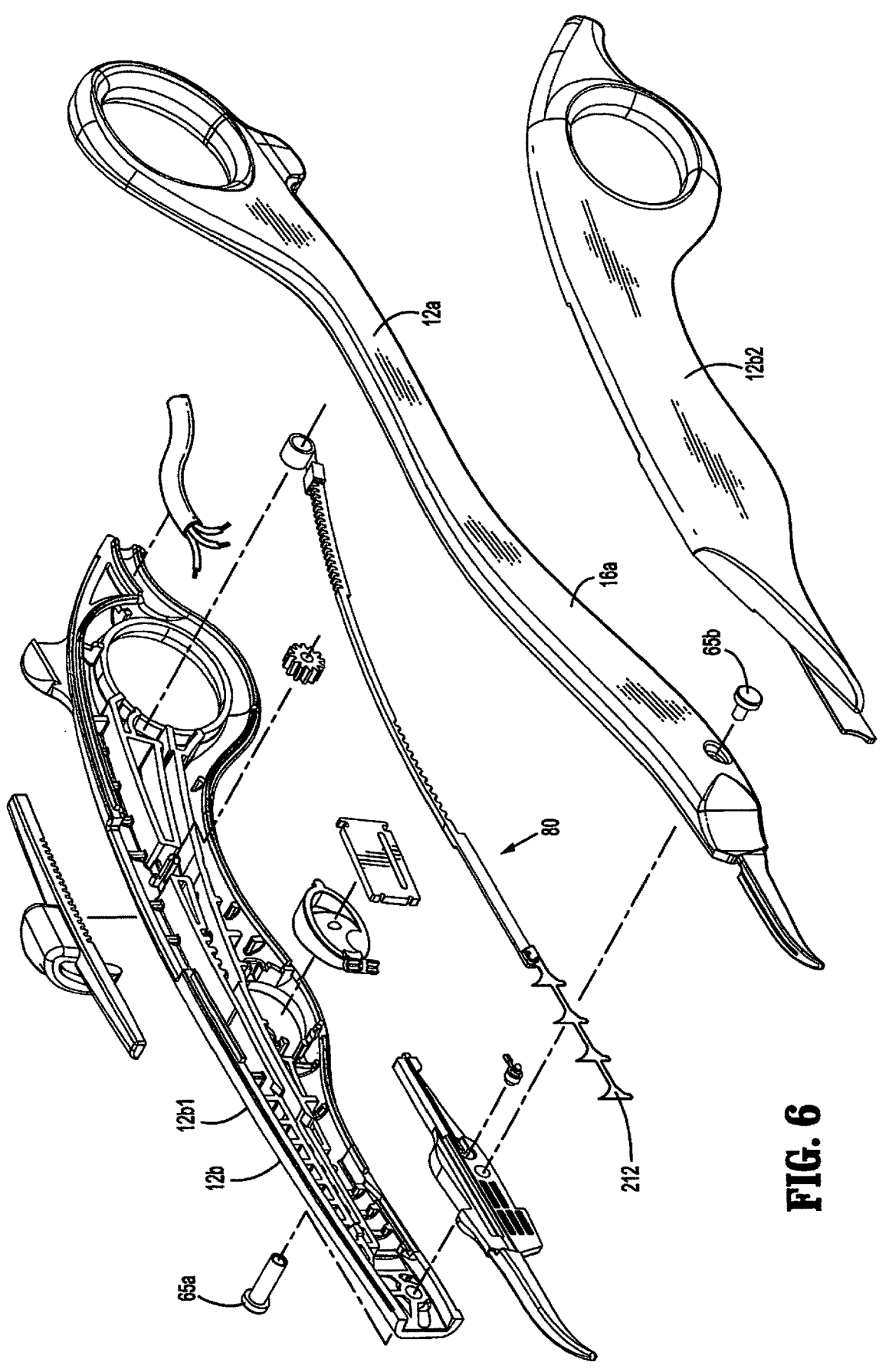
FIG. 6 is a perspective view of the forceps of FIG. 1B with parts separated.

Referring now to FIG. 6, an open bipolar forceps is configured to support blade 212. Shaft 12b is constructed from two components, namely, 12b1 and 12b2, which matingly engage one another about the distal end 16a of shaft 12a to form shaft 12b. It is envisioned that the two component halves 12b1 and 12b2 may be ultrasonically-welded together at a plurality of different weld points or the component halves 12b1 and 12b2 may be mechanically engaged in any other known fashion, snap-fit, glued, screwed, etc. After component halves 12b1 and 12b2 are welded together to form shaft 12b, shaft 12a is secured about pivot 65 and positioned within a cut-out or relief 21 defined within shaft portion 12b2 such that shaft 12a is movable relative to shaft 12b.

More particularly, when the user moves the shaft 12a relative to shaft 12b to close or open the jaw members 110 and 120, the distal portion of shaft 12a moves within cutout 21 formed within portion 12b2. Blade 212 is shown attached to cutting mechanism 80. It is envisioned that the device can be actuated to move blade 212 in a proximal and/or distal direction. Further details relating to the inter-cooperative relationships of the inner-working components of forceps 10 are disclosed in commonly-owned U.S. patent application Ser. No. 10/962,116 herein incorporated by reference in its entirety.

Figure 7A:
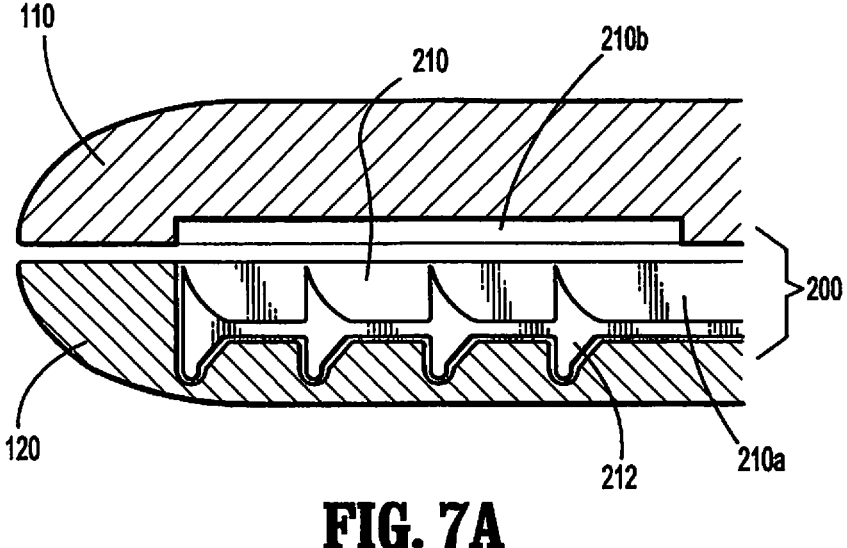
FIG. 7A is a greatly-enlarged schematic, side cross sectional view of the end effector assembly of FIG. 1A shown in a closed configuration with blade in bottom jaw.
Figure 7B:
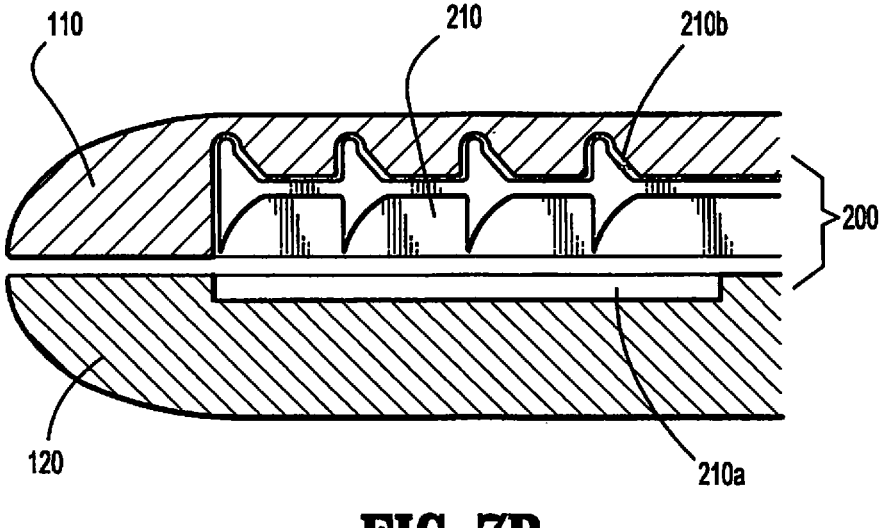
FIG. 7B is a greatly-enlarged schematic, side cross sectional view of the end effector assembly of FIG. 1A shown in a closed configuration with blade in top jaw.

Referring now to FIGS. 7A and 7B, when the blade 212 is in an unactuated position and fully recessed, it can be located within either jaw members 110 and 120. As best seen in FIG. 7A blade 212 is shown in lower jaw member 120, and the empty blade channel half 210b is disposed in jaw member 110. As best seen in FIG. 7B blade 212 is shown in upper jaw member 110, and the empty blade channel half 210a is disposed in jaw member 120. The positioning of the blade is predetermined depending upon, among other things, the needs and desires of the surgeon.

Referring now to FIGS. 8A, 8B, 8C and 8D, electrosurgical forceps for sealing tissue are shown having an upper jaw member 110 and a lower jaw member 120. Axis 850 is shown to represent that the jaw members 110, 120 are movable from a first position in spaced relation relative to one another to at least one subsequent position. Accordingly, the jaw members 110, 120 are moveable and cooperate to grasp tissue therebetween. As described above, at least one of the jaw members has a blade 210 channel defined along a length thereof. One or more of the jaw members includes a surgical blade assembly 200 including a blade channel 210 having a proximal end, a distal end and one or more troughs 220 positioned between the proximal and distal ends. A blade body 212 having a proximal end, a distal end, and a cutting edge 215 extends between the proximal and distal ends, and one or more flanges 230 are positioned opposite the cutting edge 215. As described above, the flanges 230 are disposed within the one or more troughs 220 such that the blade body 212 is in sliding communication with the blade channel 210.

Figure 8A:
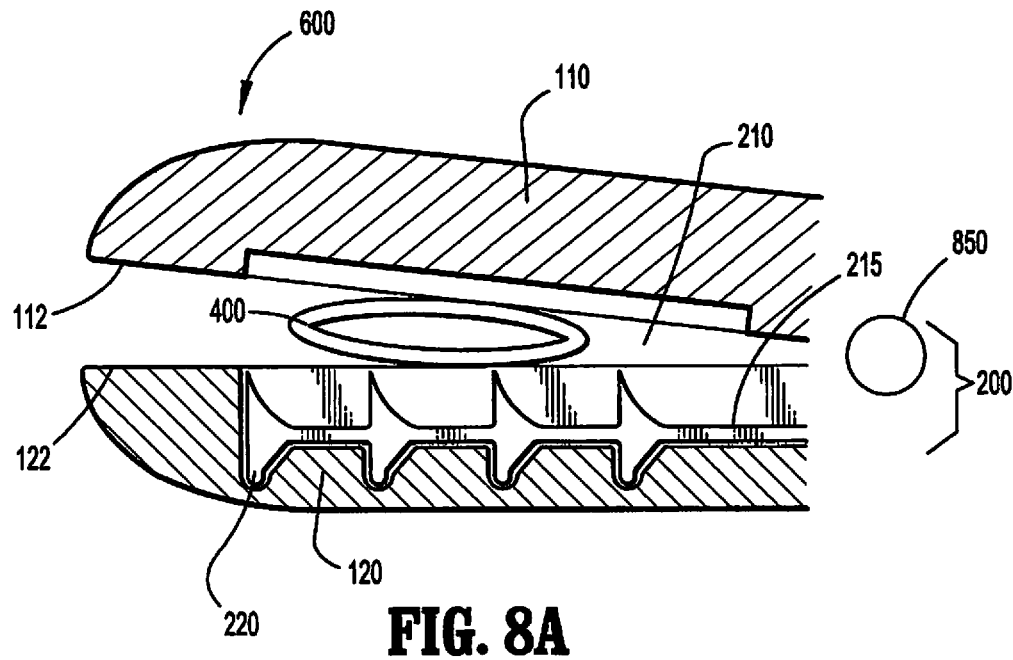
FIG. 8A is a greatly-enlarged schematic, side cross sectional view of the end effector assembly of FIG. 1A shown in an open configuration with tissue therein.

Referring now to FIG. 8A, the jaw members 110 and 120 are shown by arrow 600 being moved from a first position in spaced relation relative to one another to at least one subsequent position. As shown, the jaw members 110 and 120 are being moved to grasp tissue 400 therebetween. Each of the jaw members includes an electrically conductive sealing plate 112, 122 which communicates electrosurgical energy through tissue 400 held therebetween when the forceps is activated.

Figure 8B:
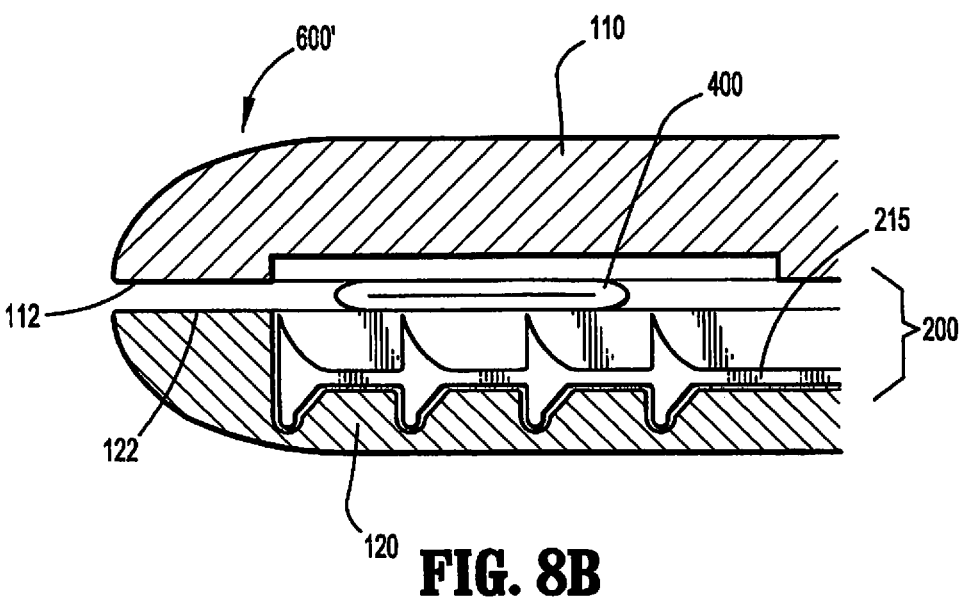
FIG. 8B is a greatly-enlarged schematic, side cross sectional view of the end effector assembly of FIG. 1A shown in a closed configuration with tissue therein.
Figure 8C:
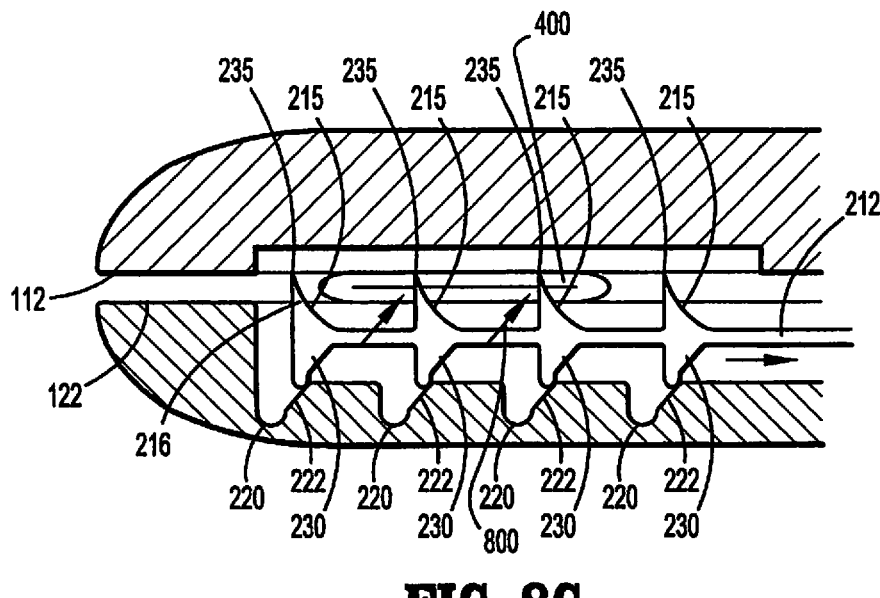
FIG. 8C is a greatly-enlarged schematic, side cross sectional view of the end effector assembly of FIG. 1A shown in a closed configuration with tissue therein during actuation.

FIG. 8B, shows jaw members 110 and 120 closing about tissue 400 in accordance with arrow 600'.

FIG. 8C, shows the blade 212 being actuated in a proximal direction. The proximal movement causes the plurality of flanges 230 to rub against the corresponding plurality of troughs 220 which result cutting point 235 puncturing tissue 400. Arrow 800 shows the direction and angle of cutting point 235 being substantially equal to the incline of proximal wall 222.

Figure 8D:
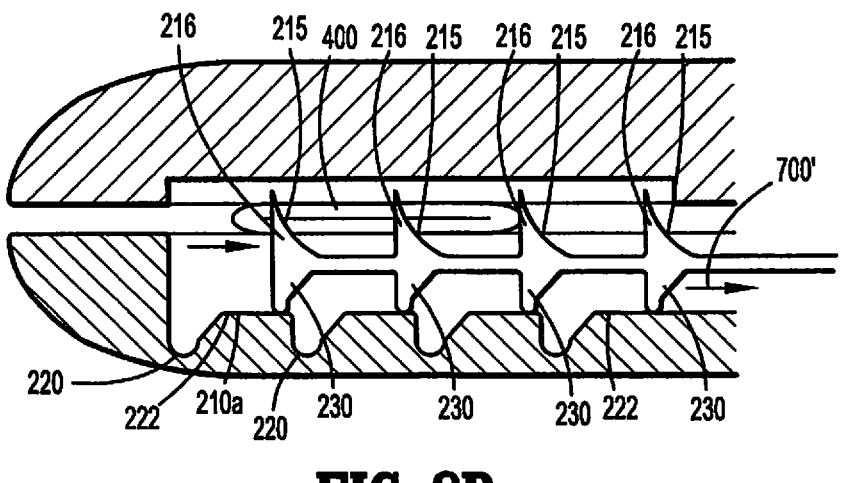
FIG. 8D is a greatly-enlarged schematic, side cross sectional view of the end effector assembly of FIG. 1A shown in a closed configuration with tissue therein during actuation.

Referring now to FIG. 8D, the blade direction is shown by arrow 700' as being actuated in a proximal direction. The proximal movement causes flange 230 to rub against blade channel 210a which results in cutting edge 215 cutting across tissue 400. Arrow 800' shows the direction of cutting teeth 216 being substantially equal to wall 222 above trough 220.

Figures 9A, 9B:
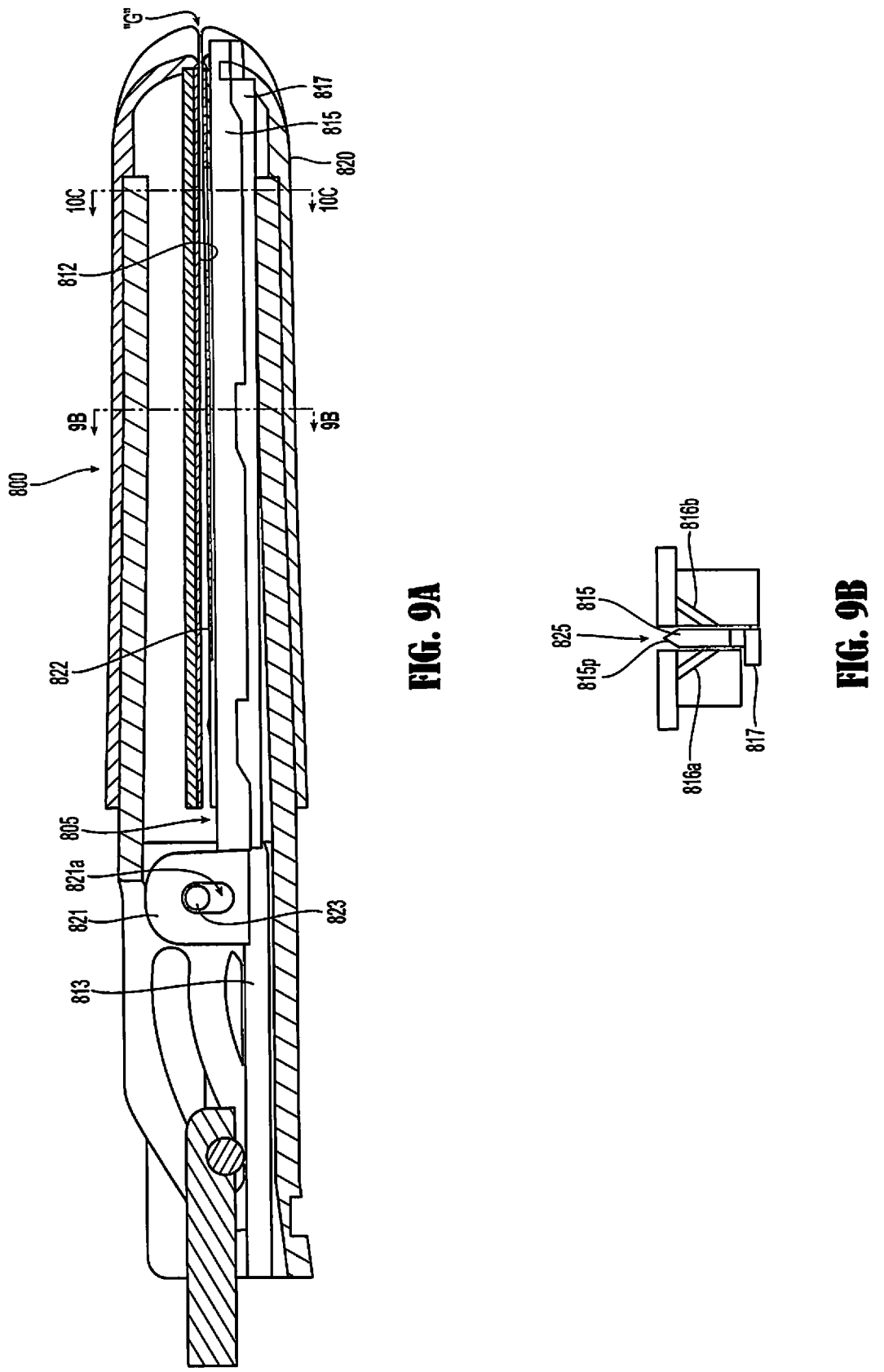
FIG. 9A is an internal, side cross sectional view of an end effector of another embodiment of the present disclosure showing an unbiased position of a cutting mechanism with a blade return.
FIG. 9B is an enlarged internal, end cross sectional view of a blade and blade camming member disposed in the unbiased position with the blade resting in a knife channel defined in the lower jaw member and below a gap "G" defined between the jaw members.

Turning now to FIG. 9A, another embodiment for an end effector 800 is shown that includes a cutting mechanism with an automatic blade return feature. End effector 800 is similar to the above-described end effector assemblies and, as such, only those elements that differ are described in detail below.

End effector assembly 800 includes upper and lower jaw members 810 and 820 each having respective electrically conductive sealing surfaces 812 and 822 disposed in general opposition relative to one another when closed about tissue (FIG. 9A). Electrically conductive sealing surface 822 of lower jaw member 820 includes a blade channel 825 defined longitudinally therealong configured to house a cutting mechanism 805 therein. Cutting mechanism 805 includes a blade 815 having a proximal flange 821 coupled to a proximal end of jaw member 820 about a slide pin 823. Blade 815, upon actuation thereof, is configured to move atop slide pin 823 in a normal direction relative to electrically conductive sealing surface 822 upon actuation thereof via actuation rod 813.

Figures 10A, 10B, 10C:
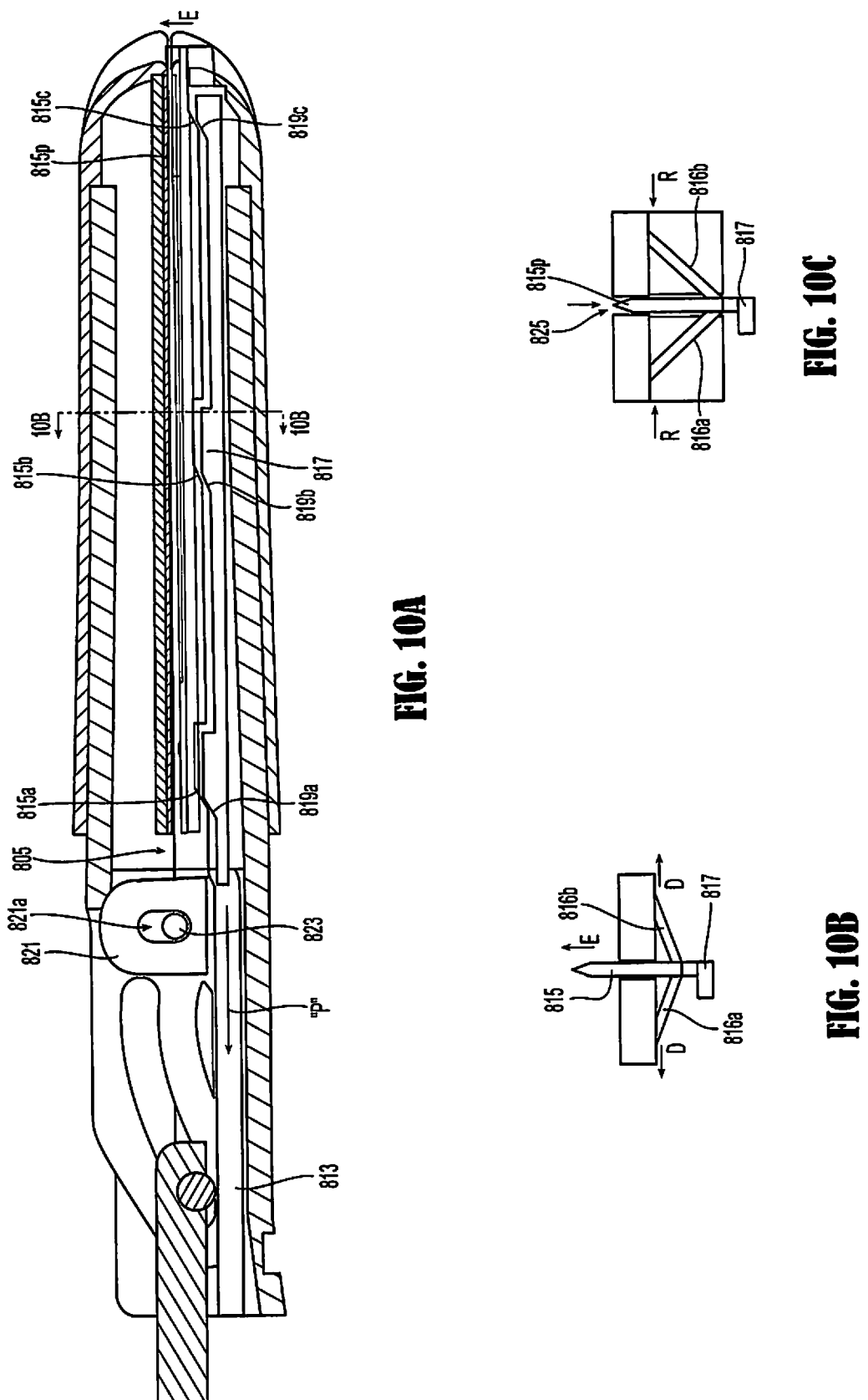
FIG. 10A is an internal, side cross sectional view of the end effector of FIG. 9A with the blade camming member moved proximally to cam the blade from the knife channel and into the gap "G" between the jaw members.
FIG. 10B is an enlarged internal, end cross sectional view of the blade deployed into the gap "G" with a pair of blade return springs biased against an underside of the lower jaw member.
FIG. 10C is an enlarged internal, end cross sectional view of the blade resetting within the knife channel upon release of the blade camming member.

Actuation rod 813 is disposed in the proximal end of the jaw member 820 and is configured to operably connect to a blade cam 817 disposed below and in vertical registration with blade 815 such that movement of the actuation rod 813, in turn, forces blade 815 into the gap "G" defined between the jaw members 810, 812 to cut tissue. More particularly, blade cam 817 includes a series of cam surfaces 819a-819c that are configured to operably engage a corresponding series of camming slots 815a-815c defined within blade 815 such that proximal movement of the actuation rod 813 in direction "P" moves the blade cam 817 proximally to force the camming surfaces 819a-819c into engagement with the camming slots 815a-815c to extend the blade 815 into gap "G" in the direction "E" to cut tissue (FIG. 10A). Camming surfaces 819a-819c of different angles are envisioned to allow more or less aggressive extension of the blade into gap "G".

Configuring the angle of engagement has varying advantages and disadvantages and may be designed for different purposes or different instrument configurations. For example, the more aggressive the angle, the less movement of the actuation rod 813 to cut tissue but more force is required to move the actuation rod 813. Lessening the angle reduces the actuation force but lengthens the stroke of the actuation rod 813 which may limit the design of the actuator (not shown). An angle of about forty-five degrees (45°) is contemplated as a compromise angle which tends to provide a tolerable and repeatable actuation force and limit the stroke of the actuation rod to about 0.02-0.03 inches.

FIG. 9B is a schematic cross section of FIG. 9A taken along line 9B of FIG. 9A showing the blade cam 817b disposed within respective camming slot 815b and the blade recessed relative to gap "G". Blade 815 includes a pair of blade springs or living hinges 816a and 816b disposed on either side thereof and which are each configured to engage and bias against an underside of electrically conductive sealing surface 822 of lower jaw member 820. Blade springs 816a, 816b are configured to return the blade 815 to a recessed position within blade channel 825 when actuation rod 813 is released.

FIG. 10B is a schematic representation of the movement of the blade 815 upon actuation of rod 813 in the direction "P". More particularly and as referenced above, proximal movement of the actuation rod 813 in direction "P" moves the blade cam 817 proximally to force the camming surfaces 819a-819c into engagement with the camming slots 815a-815c to extend the blade 815 into gap "G" in the direction "E" to cut tissue (FIG. 10A). As the camming surfaces 819a-819c engage the camming slots 815a-815c the blade springs 816a-816b bias outwardly against the underside of electrically conductive sealing surface 822 of lower jaw member 820 in the direction "D". Edge 815p of blade 815 sever tissue disposed in blade slot 825 therealong.

Upon release (or movement distally) of actuation rod 813, the camming surfaces 819a-819c disengage from camming slots 815a-815c and re-settle therein thereby resetting blade 815 within blade channel 825. More particularly, blade springs 816a, 816b bias the blade 815 back into the blade channel 825 as the blade springs 816a, 816b move inwardly in the direction "R" (FIG. 10C).

As best seen in FIGS. 9A and 10A and as mentioned above, movement of the blade 815 into blade channel 825 is generally vertical. As a result thereof, the slot 821a defined in the proximal end 821 of the blade 815 guides the blade 815 to slide vertically along slide pin 823 when the blade 815 is actuated. Slot 821a may be configured in any fashion to alter the movement of the blade into and out of blade channel 825 depending upon a particular purpose. For example, the slot 821a may be angled to promote both vertical and horizontal movement of the blade 815 to sever tissue in a more effective manner depending upon blade type, e.g., serrated.

It is envisioned that the end effector may include a blade lockout mechanism that is configured to prevent the jaw members 810, 820 from opening when the actuation rod 813 is actuated and the blade 815 is deployed to sever tissue. For example, the slide pivot 823 may be configured to lock the jaw members 810, 820 in place upon actuation thereof. Other lockout mechanisms are also contemplated.

From the foregoing and with reference to the various figure drawings, those skilled in the art will appreciate that certain modifications can also be made to the present disclosure without departing from the scope of the same. For example, although the proximal motion of the cutting path has been described, it is contemplated the troughs may be reversed so that the distal wall of trough 220 may be configured as a ramp with curvature or without curvature. Accordingly, distal actuation of the blade may be incorporated within blade channel depending upon a particular purpose and/or to facilitate manipulation by a user. Here, a user could push the blade through tissue instead of pulling it by proximal activation as described herein.

What is claimed is:

1. A forceps, comprising:
a pair of jaw members movable from a first position in spaced relation relative to one another to at least one subsequent position wherein the jaw members cooperate to grasp tissue in a gap therebetween;
at least one of the jaw members having a blade channel defined therein configured to house a cutting mechanism therein, the cutting mechanism including:
a blade having a series of camming slots defined along a length thereof, the blade including at least one blade spring operably associated therewith configured to bias the blade to a recessed position within the blade channel; and
a blade cam disposed in general vertical registration with the blade, the blade cam including a series of camming surfaces configured to operably engage the corresponding series of camming slots of the blade, the blade cam including a proximal end operably coupled to an actuation rod configured to move the blade cam upon proximal movement thereof;
wherein, actuation of the actuation rod moves the camming surfaces of the blade cam into engagement against the camming slots forcing the blade into the gap between the jaw members in a vertical direction away from the actuation rod and against the bias of the at least one blade spring to cut tissue therebetween.

2. The forceps according to claim 1, wherein upon release of the actuation rod, the bias of the at least one blade spring returns the blade to the recessed position within the blade channel.

3. The forceps according to claim 1, wherein the at least one jaw member includes a tissue engaging surface disposed thereon that defines the blade channel therein and wherein the at least one blade spring engages an underside of the tissue engaging surface to bias the blade to the recessed position within the blade channel upon actuation of the actuation rod.

4. The forceps according to claim 3, wherein the at least one blade spring of the blade comprises two blade springs on either side thereof that are each configured to engage the underside of the tissue engaging surface of the at least one jaw member upon actuation of the actuation rod.

5. The forceps according to claim 3, wherein the at least one blade spring of the blade comprises a plurality of blade springs on either side thereof that are each configured to engage the underside of the tissue engaging surface of the at least one jaw member upon actuation of the actuation rod.

6. The forceps according to claim 1, wherein the bias of the at least one blade spring operates to return the actuation rod distally upon release of the actuation rod.

7. The forceps according to claim 1, wherein the blade includes a proximal end defining a slot therein configured to slide atop a pin operably associated with the at least one jaw member, the slot and pin arrangement configured to control the movement of the blade into the gap between the jaw members upon actuation of the actuation rod.

8. The forceps according to claim 7, wherein the slot and pin arrangement controls movement of the blade into the blade channel in a vertical direction towards the other jaw member.

9. The forceps according to claim 7, wherein the slot and pin arrangement moves the blade both vertically and horizontally within the blade channel relative to the other jaw member to cut tissue disposed between the jaw members.

10. An electrosurgical forceps, comprising:

a pair of jaw members movable from a first position in spaced relation relative to one another to at least one subsequent position wherein the jaw members cooperate to grasp tissue in a gap therebetween;

each of the jaw members including an electrically conductive sealing plate adapted to connect to an energy source and configured to communicate energy through tissue held therebetween; and at least one of the jaw members having a blade channel defined therein configured to house a cutting mechanism therein, the cutting mechanism including:

a blade having a series of camming slots defined along a length thereof, the blade including at least one blade spring operably associated therewith configured to bias the blade to a recessed position within the blade channel; and a blade cam disposed in general vertical registration with the blade, the blade cam including a series of camming surfaces configured to operably engage the corresponding series of camming slots of the blade, the blade cam including a proximal end operably coupled to an actuation rod configured to move the blade cam upon proximal movement thereof;

wherein, actuation of the actuation rod moves the camming surfaces of the blade cam into engagement against the camming slots forcing the blade into the gap between the jaw members in a vertical direction away from the actuation rod and engaging the at least one blade spring against an underside of the electrically conductive sealing plate of the at least one jaw member to cut tissue disposed between the jaw members and wherein, upon release of the actuation rod, the bias of the at least one blade spring returns the blade to the recessed position within the blade channel.

11. The forceps according to claim 10, wherein the at least one blade spring of the blade comprises two blade springs on either side thereof that are each configured to engage the underside of the electrically conductive sealing plate of the at least one jaw member upon actuation of the actuation rod.

12. The forceps according to claim 10, wherein the at least one blade spring of the blade comprises a plurality of blade springs on either side thereof that are each configured to engage the underside of the electrically conductive sealing plate of the at least one jaw member upon actuation of the actuation rod.

13. The forceps according to claim 10, wherein the blade includes a proximal end defining a slot therein configured to slide atop a pin operably associated with the at least one jaw member, the slot and pin arrangement configured to control the movement of the blade into the gap between the jaw members upon actuation of the actuation rod.

14. The forceps according to claim 13, wherein the slot and pin arrangement controls movement of the blade into the blade channel in a vertical direction towards the other jaw member.

15. The forceps according to claim 13, wherein the slot and pin arrangement moves the blade both vertically and horizontally within the blade channel relative to the other jaw member to cut tissue disposed between the jaw members.

16. A forceps, comprising:

a pair of jaw members movable from a first position in spaced relation relative to one another to at least one subsequent position wherein the jaw members cooperate to grasp tissue in a gap therebetween;

at least one of the jaw members having a blade channel defined therein configured to house a cutting mechanism therein, the cutting mechanism including:

a blade having a series of camming slots defined along a length thereof, the blade including at least one pair of blade springs disposed on either side thereof that are each configured to engage the underside of the tissue engaging surface of the at least one jaw member upon actuation of the actuation rod to bias the blade to a recessed position within the blade channel; and a blade cam disposed in general vertical registration with the blade, the blade cam including a series of camming surfaces configured to operably engage the corresponding series of camming slots of the blade, the blade cam including a proximal end operably coupled to an actuation rod configured to move the blade cam upon proximal movement thereof;

wherein, actuation of the actuation rod moves the camming surfaces of the blade cam into engagement against the camming slots forcing the blade into the gap between the jaw members in a vertical direction away from the actuation rod and against the bias of the at least one pair of blade springs to cut tissue therebetween.

17. The forceps according to claim 16, wherein the at least one pair of blade springs of the blade comprises a plurality of pairs of blade springs disposed along a length thereof.

18. The forceps according to claim 16, wherein the bias of the pair of blade springs operates to return the actuation rod distally upon release of the actuation rod.

* * * * *